United States Patent [19]

Durant et al.

[11] 4,333,946
[45] Jun. 8, 1982

[54] BLOCKING HISTAMINE H₂-RECEPTORS WITH IMIDAZOLYLALKYL GUANIDINE DERIVATIVES

[75] Inventors: Graham J. Durant; Charon R. Ganellin, both of Welwyn Garden City; Geoffrey R. Owen, High Wycombe; Rodney C. Young, Bengeo, all of England

[73] Assignee: Smith Kline & French Laboratories Limited, Welwyn Garden City, England

[21] Appl. No.: 229,435

[22] Filed: Jan. 29, 1981

Related U.S. Application Data

[62] Division of Ser. No. 70,184, Aug. 27, 1979, Pat. No. 4,276,301, which is a division of Ser. No. 892,232, Mar. 31, 1978, Pat. No. 4,192,879, which is a division of Ser. No. 686,185, May 13, 1976, Pat. No. 4,098,898.

[30] Foreign Application Priority Data

May 21, 1975 [GB] United Kingdom ............... 21817/75
Nov. 20, 1975 [GB] United Kingdom ............... 47782/75

[51] Int. Cl.³ ................. A61K 31/415; C07D 233/64; C07D 233/68
[52] U.S. Cl. .................................. 424/273 R; 548/301; 548/315; 548/321; 548/337; 548/342
[58] Field of Search ............... 548/342, 301, 315, 321, 548/337; 424/273 R

[56] References Cited

U.S. PATENT DOCUMENTS

| | | | |
|---|---|---|---|
| 3,808,336 | 4/1974 | Durant et al. | 548/342 X |
| 3,868,457 | 2/1975 | Black et al. | 424/273 R |
| 3,950,333 | 4/1976 | Durant et al. | 424/273 R X |
| 3,950,353 | 4/1976 | Durant et al. | 424/273 R X |
| 3,953,460 | 4/1976 | Durant et al. | 424/273 R X |
| 3,968,216 | 7/1976 | Black et al. | 424/263 |
| 3,968,227 | 7/1976 | Durant et al. | 548/342 X |
| 3,979,398 | 9/1976 | White | 548/342 X |
| 4,000,296 | 12/1976 | Durant et al. | 424/273 R X |
| 4,000,302 | 12/1976 | Black et al. | 424/273 R |
| 4,034,101 | 7/1977 | Durant et al. | 424/273 R |
| 4,046,907 | 9/1977 | Durant et al. | 548/342 X |
| 4,109,003 | 8/1978 | Durant et al. | 424/273 R |
| 4,124,717 | 11/1978 | Durant et al. | 424/270 |
| 4,152,443 | 5/1979 | Durant et al. | 424/273 R |
| 4,165,377 | 8/1979 | Jones et al. | 424/270 |
| 4,165,378 | 8/1979 | Gilman et al. | 424/270 |

FOREIGN PATENT DOCUMENTS 816850 12/1974 Belgium .
2211454 10/1972 Fed. Rep. of Germany .
1305549 2/1973 United Kingdom .

OTHER PUBLICATIONS

Derwent Abstract 30208S (Belgian 758,146).
Derwent Abstract 00068X (Belgian 830,272).

*Primary Examiner*—Richard A. Schwartz
*Attorney, Agent, or Firm*—Joan S. Keps; Richard D. Foggio; Alan D. Lourie

[57] ABSTRACT

The compounds are novel N-substituted-N'-heterocyclic alkylthioureas, guanidines and 1-nitro-2,2-diaminoethylene compounds which are histamine H₂-antagonists.

8 Claims, No Drawings

BLOCKING HISTAMINE H₂-RECEPTORS WITH IMIDAZOLYLALKYL GUANIDINE DERIVATIVES

This is a division of application Ser. No. 070,184 filed Aug. 27, 1979, now U.S. Pat. No. 4,276,301, which is a division of application Ser. No. 892,232 filed Mar. 31, 1978, now U.S. Pat. No. 4,192,879, which is a division of application Ser. No. 686,185 filed May 13, 1976, now U.S. Pat. 4,098,898.

This invention relates to pharmacologically active compounds, to methods for preparing these compounds, to pharmaceutical compositions containing these compounds and to methods of blocking histamine H₂-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine is a typical example, and diphenhydramine and chlorpheniramine are other examples are mediated through histamine H₁-receptors (Ash and Schild, *Brit. J. Pharmac. Chemother,* 27, 427, (1966)). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine H₂ receptors. Thus histamine H₂-receptors may be defined as those histamine receptors which are not blocked by mepyramine but are blocked by burimamide. Compounds which block histamine H₂-receptors are referred to as histamine H₂-antagonists.

Blockade of histamine H₂-receptors is of utility in inhibiting the biological actions of histamine which are not inhibited by "antihistamines". Histamine H₂-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example inflammation and in inhibiting the actions of histamine on blood pressure, a combination of histamine H₁- and H₂-antagonists is useful. The compounds of this invention are histamine H₂-antagonists. These compounds are represented by the following formula:

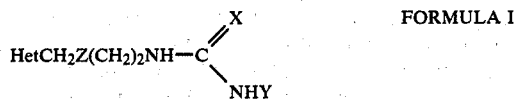

FORMULA I wherein X is sulphur, CHNO₂, N.CN or NH; Y is amino, lower alkylamino, di(lower alkyl)amino, lower alkoxy, phenylethyl, imidazolylethyl, allyl, 2,2,2-trifluoroethyl or (CH₂)$_n$R: Z is sulphur or methylene: Het is an imidazole, pyridine, thiazole, isothiazole, oxazole, isoxazole, triazole or thiadiazole ring which ring is optionally substituted by lower alkyl, hydroxy, halogen or amino; n is an integer of from 1 to 12: and R is hydroxy, lower alkoxy, amino or lower alkylamino: provided that when X is NH, Y is 2,2,2-trifluoroethyl or (CH₂)$_n$R and that when X is N.CN, Y is not amino or lower alkylamino, or a pharmaceutically acceptable acid addition salt thereof.

It will be understood that the structure illustrated in Formula I is only one of several possible representations and that other tautomeric forms are also covered by the present invention. Throughout the present specification by the terms "lower alkyl" and "lower alkoxy", we mean alkyl and alkoxy groups containing from 1 to 4 carbon atoms.

In one preferred group of compounds X is sulphur, CHNO₂ or N.CN. Y is preferably amino, allyl, 2,2,2-trifluoroethyl, (CH₂)$_n$OH or (CH₂)$_n$NH₂. Z is preferably sulphur and particularly useful compounds are those wherein Het is imidazole, pyridine, thiazole or isothiazole optionally substituted by methyl, hydroxyl, chloro or bromo, for example 4-methyl-4-imidazolyl and 2-thiazolyl.

Specific compounds falling within the scope of the present invention include:

N-cyano-N'-methoxy-N''-[2-((4-methyl-5-imidazolyl)methylthio)ethyl]guanidine,

N-cyano-N'-(2,2,2-trifluoroethyl)-N''-[2-((4-methyl-5-imidazolyl)methylthio)ethyl]guanidine, 1-nitro-2-hydrazino-2-[2-((4-methyl-5-imidazolyl)methylthio)ethylamino]ethylene, 1-nitro-2-(2,2,2-trifluoroethylamino)-2-[2-((4-methyl-5-imidazolyl)methylthio)ethylamino]ethylene, 1-nitro-2-(2,2,2-trifluoroethylamino)-2-[2-(2-thiazolyl)methylthio)ethylamino]ethylene, N-cyano-N'-(2-hydroxyethyl)-N''-[2-((4-methyl-5-imidazolyl)methylthio)ethyl]guanidine, N-cyano-N'-(2-aminoethyl)-N''-[2-((4-methyl-5-imidazolyl)methylthio)ethyl]guanidine, N-cyano-N'-(2-phenylethyl)-N''-[2-((4-methyl-5-imidazolyl)methylthio)ethyl]guanidine, N-cyano-N'-[2-(4-imidazolyl)ethyl]-N''-[2-((4-methyl-5-imidazolyl)methylthio)ethyl]guanidine, N-[2-(4-imidazolyl(ethyl]-N'-[2-((4-methyl-5-imidazolyl)methylthio)ethyl]thiourea, N-cyano-N'-[2-methoxyethyl)-N''-[4-methyl-5-imidazolyl)methylthio)ethyl]guanidine, N-cyano-N'-(7-aminoheptyl)-N''-[2-((4-methyl-5-imidazolyl)methylthio)ethyl]guanidine, N-cyano-N'-(8-aminooctyl)-N''-[2-((4-methyl-5-imidazolyl)methylthio)ethyl]guanidine, N-cyano-N'-(4-hydroxybutyl)-N''-[2-((4-methyl-5-imidazolyl)methylthio)ethyl]guanidine, N-(2-aminoethyl)-N'-[2-((4-methyl-5-imidazolyl)methylthio)ethyl]guanidine, N-cyano-N'-allyl-N''-[2-((4-methyl-5-imidazolyl)methylthio)ethyl]guanidine and N-cyano-N'-(2-methylaminoethyl)-N''-[2-((4-methyl-5-imidazolyl)methylthio)ethyl]guanidine.

The compounds of Formula I may be prepared from amines of the following Formula II:

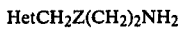

FORMULA II wherein Het, Z, m and n have the same significance as in Formula I.

For the production of those compounds of Formula I, wherein X is CHNO₂, N.CN or NH, the amino of Formula II is reacted with a compound of formula III:

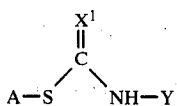
FORMULA III wherein $X^1$ is $CHNO_2$, $N.CN$ or $N.COC_6H_5$, Y has the same significance as in Formula I and A is lower alkyl. The compound of Formula III is in turn produced from the reaction of a compound of Formula IV:

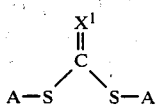
FORMULA IV wherein $X^1$ and A have the same significance as in Formula III with an amine of formula $YNH_2$. Alternatively, when $X^1$ is $CHNO_2$, a compound of Formula IVa may be used:

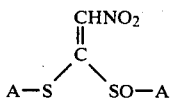
FORMULA IVa

In certain cases it may be convenient first to react the compound of Formula IV with the amine of Formula II to give a compound of Formula V:

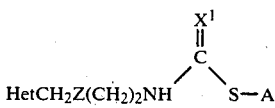
FORMULA V wherein Het, Z, $X^1$ and A have the above significance and then to react the compound of Formula V with the amine of formula $YNH_2$. This is particularly preferred when Y is amino, aminoalkyl or hydroxyalkyl.

For the production of those compounds wherein X is NH the compound prepared by the above method wherein $X^1$ is $N.CO\ C_6H_5$ or $N.CN$ is subjected to hydrolysis.

Those compounds of Formula I wherein X is sulphur, may be prepared by the reaction of dithiocarbamic ester of Formula VI:

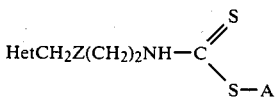
FORMULA VI wherein Het and Z, have the same significance as in Formula I and A is lower alkyl.

All the above processes may thus be summarised by the following reaction

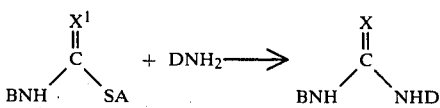

wherein either B is $HetCH_2Z(CH_2)_2$ and D is Y or B is Y and D is $HetCH_2Z(CH_2)_2$ the product of the reaction wherein $X^1$ is $N.COC_6H_5$ being submitted to acid hydrolysis to yield the compound wherein X is NH.

Alternatively the compounds of Formula I wherein X is sulphur may be prepared by the reaction of an isothiocyanate of Formula VII:

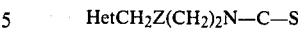

FORMULA VII with an amine of formula $YNH_2$ wherein Y has the same significance as in Formula I.

Alternatively, the amine of Formula II may be reacted with an isothiocyanate of formula Y-N-C-S.

The compounds of Formula I block histamine $H_2$-receptors, that is they inhibit the biological action of histamine which are not inhibited by "antihistamines" such as mepyramine but are inhibited by burmamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity. In conventional tests such as the rat paw oedema test, where the oedema is induced by an irritant, the rat paw volume is reduced by suncutaneous injection of doses of a compound of Formula I. In a conventional test, such as the measurement of blood pressure in the anaesthetized rat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula I or a pharmaceutically acceptable acid addition salt thereof and methods of blocking histamine $H_2$-receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimed will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following examples.

EXAMPLE 1

N-Cyano-N'-methoxy-N''-[2-(4-methyl-5-imidazolyl)-methylthio)ethyl]guanidine

A solution of methoxamine (7.0 g), prepared from the hydrochloride and potassium hydroxide in methanol (50 ml) and water (10 ml) was added to a solution of dimethylcyanodithioimidocarbonate (7.3 g) in methanol (40 ml) and stirred at room temperature for 60 hours. A solution of 4-methyl-5-[(2-aminoethyl)thiomethyl]imidazole (8.6 g) in methanol (30 ml) was added and the resulting solution was heated under reflux for 18 hours. Concentration followed by chromatographic purification on a column of silica gel with chloroform-methanol (10:1) as eluant and final recrystallisation from acetonitrile afforded the title compounds m.p. 155°-6°

(Found: C, 45.0; H, 5.9; N, 31.3; S, 11.9%; $C_{10}H_{16}N_6OS$. requires: C, 44.8; H, 6.0; N, 31.3; S, 11.9%).

EXAMPLE 2

N-Cyano-N'-[2-((4-methyl-5-imidazolyl)methylthio)ethyl]-N''-(2,2,2-trifluoroethyl)guanidine A solution of 2,2,2-trifluoroethylamine (9.9 g), prepared from the hydrochloride and potassium hydroxide in methanol (50 ml) and water (10 ml) was added to a solution of dimethylcyanodithioimidocarbonate (7.3 g) in methanol (40 ml) and stirred at room temperature for 90 hours. Concentration gave a colourless solid that was washed with chloroform and then dissolved in methanol (40 ml). A solution of 4-methyl-5-[(2-aminoethyl)-thiomethyl]imidazole (3.8 g) in methanol was added and the resulting solution was heated under reflux for 20 hours. Concentration followed by chromatographic purification on a column of silica gel with chloroform-methanol (15:1) as eluant and final recrystallisation from acetonitrile gave the title compound (0.85 g), m.p. 155°-6°.

(Found: C, 41.3; H, 4.7; N, 26.3; S, 10.1%; $C_{11}H_{15}F_3N_6S$. requires: C, 41.2; H, 4.7; N, 26.2; S, 10.0%).

EXAMPLE 3

1-Nitro-2-hydrazino-2-[2-((4-methyl-5-imidazolyl)methylthio)ethylamino]ethylene

Hydrazine hydrate (1.5 g) was added to a solution of 1-nitro-2-methylthio-2-[2-(4-methyl-5-imidazolyl)methylthio)ethylamino]ethylene (4.7 g) in warm ethanol (200 ml) and the solution was set aside overnight at room temperature. Concentration, followed by recrystallisation of the product from acetonitrile afforded the title compound (2.9 g), m.p. 141.5°-142.5°.

(Found: C, 39.6; H, 6.0; N, 31.0; S, 11.7%; $C_9H_{16}N_6O_2S$ requires: C, 39.7; H, 5.9; N, 30.9; S, 11.8%).

EXAMPLE 4

1-Nitro-2-[2-((4-methyl-5-imidazolyl)methylthio)ethylamino]-2-(2,2,2-trifluoroethylamino)ethylene A solution of 2,2,2-trifluoroethylamine (4.0 g) from the hydrochloride and potassium hydroxide in methanol (45 ml) and water (5 ml) was added slowly to a suspension of 1-nitro-2-methylsulphinyl-2-methylthio ethylene (3.6 g) in methanol (150 ml) at 0°. The mixture was stirred at room temperature for 24 hours, concentrated and dissolved in chloroform. Filtration, redissolution in a small volume of chloroform and precipitation with hexane afforded an orange crystalline solid. This was dissolved in methanol (25 ml) and a solution of 4-methyl-5-[(2-aminoethyl)thiomethyl]imidazole (2.1 g) in methanol (25 ml) was added. The resulting solution was heated under reflux for 2 hours and set aside at room temperature for 18 hours. Concentration followed by chromatographic purification on a column of silica gel with chloroform-methanol (15.1) as eluant and final crystallisation from ethanol afforded the title compound as a hemi-ethanolate (2.4 g) m.p. 161° (dec).

(Found: C, 39.8; H, 5.2; N, 19.3; S, 9.2%; $C_{11}H_{16}F_3N_5O_2S.0.5C_2H_5OH$ requires: C, 39.8; H, 5.3; N, 19.3; S, 8.9%).

EXAMPLE 5

N-Cyano-N'-(2-hydroxyethyl)-N''-[2-((4-methyl-5-imidazolyl)methylthio)ethyl]guanidine A solution of N-cyano-N'-[2-((4-methyl-5-imidazolyl)methylthio)ethyl]-S-methylisothiourea (2.7 g) (British Specification No. 1397436) and ethanolamine (1.34 g) in ethanol (50 ml) was heated under reflux for 19 hours. Concentration followed by chromatographic purification on a column of silica gel with chloroform-methanol (10:1) as eluant and final recrystallisation from isopropyl alcohol—acetonitrile gave the title compound, m.p. 146°-7°

(Found: C, 46.8; H, 6.5; N, 29.6; S, 11.2% $C_{11}H_{18}N_6OS$; requires: C, 46.8; H, 6.4; N, 29.8; S, 11.4%).

EXAMPLE 6

N-Cyano-N'-[2-((4-methyl-5-imidazolyl)methylthio)ethyl]-N''-(2-phenylethyl)guanidine

A solution of N-cyano-N'-[2-((4-methyl-5-imidazolyl)methylthio)ethyl]-S-methylisothiourea (2.69 g) and 2-phenylethylamine (7.2 g) in acetonitrile (50 ml) was heated under reflux for 24 hours. Following concentration and ether extraction to remove excess 2-phenylethylamine the crude product was chromatographed on a column of silica gel and eluted with ethyl acetate-isopropyl alcohol (4:1). Recrystallisation from ethanol-ether afforded the title compound (1.4 g) m.p. 135°–136°.

(Found: C, 59.8; H, 6.8; N, 24.8; S, 9.4% $C_{17}H_{22}N_6S$ requires: C, 59.6; H, 6.5; N, 24.5; S, 9.4%).

EXAMPLE 7

N-Cyano-N'-[2-(4-imidazolyl)ethyl]-N''-[2-((4-methyl-5-imidazolyl)methylthio)ethyl]guanidine

A mixture of N-cyano-N'-[2-((4-methyl-5-imidazolyl)methylthio)ethyl]-S-methylisothiourea (8.07 g) and bistamine base (3.36 g) was heated for 3 hours at 100° and then for 3 hours at 130°–140°. The product was chromatographed on a column of silica gel with ethyl acetate/isopropyl alcohol (5:1) as eluent and crystallised by slow evaporation from isopropyl alcohol. Recrystallisation from water afforded the title compound, m.p. 170°–171°.

(Found: C, 50.3; H, 6.2; N, 33.5; S, 9.7%; $C_{14}H_{20}N_8S$ requires: C, 50.6; H, 6.1; N, 33.3; S, 9.7%).

EXAMPLE 8

1-Nitro-2-(2,2,2-trifluoroethylamino)-2-[2-(2-thiazolylmethylthio)ethylamino]ethylene

When, in the procedure of Example 4, 2-[(2-aminoethyl)thiomethyl]thiazole is reacted with the product obtained from the reaction of 2,2,2-trifluoroethylamine and 1-nitro-2-methylsulphinyl-2-methylthioethylene the title compound, m.p. 119°–120° (from ethyl acetate) is produced.

(Found: C, 35.4; H, 3.8; N, 16.3; S, 18.7% $C_{10}H_{13}F_3N_4O_2S_2$ requires: C, 35.1; H, 3.8; N, 16.4; S, 18.7%).

EXAMPLE 9

N-[2-(4-imidazolyl)ethyl]-N''-[2-((4-methyl-5-imidazolyl)methylthio)ethyl]thiourea

Sodium ethoxide solution (prepared from 0.46 g sodium in ethanol) was added to a solution of S-methyl-N'-[2-((4-methyl-5-imidazolyl)methylthio)ethyl]dithiocarbonate hydriodide (7.8 g) in ethanol. Histamine base (2.2 g) was added and the solution was heated under reflux for 48 hours. Concentration followed by chromatographic purification of the product on a column of silica gel with ethyl acetate followed by isopropyl alcohol as eluent afforded the title compound as a glass containing water and isopropyl alcohol.

(Found: C, 46.3; H, 6.3; N, 23.6% $C_{13}H_{20}N_6S_2 + 4\%$ $C_3H_7OH + 4.5\%$ $H_2O$ requires: C, 46.6; H, 6.5; N, 23.7%)

EXAMPLE 10

N-cyano-N'-(2-aminoethyl)-N''-[2-((4-methyl-5-imidazolyl)methylthio)ethyl]guanidine

Reaction of N-cyano-N'-[2-((4-methyl-5-imidazolyl)methylthio)ethyl]-S-methylisothiourea with excess ethylenediamine at room temperature afforded the title compound m.p. 164°–167° (from acetonitrile-ethanol)

(Found: C, 46.9; H, 6.5; N, 35.1; S, 11.1% $C_{11}H_{19}N_7S$ requires: C, 47.0; H, 6.8; N, 34.8; S, 11.4%).

EXAMPLE 11

N-Cyano-N'-(2-methoxyethyl)-N''-[2-((4-methyl-5-imidazolyl)methylthio)ethyl]guanidine

N-Cyano-N'-[2-((4-methyl-5-imidazolyl)methylthio)ethyl]-S-methylisothiourea (4.05 g) was dissolved in 2-methoxyethylamine (15 ml) and heated under reflux for 6 hours. Evaporation of the solvent and chromatographic purification of the residue on a column of silica gel with elution by chloroform and then with chloroform/methanol (20:1) yielded the title compound as a pale yellow oil (2.7 g).

(Found: C, 47.8; H, 7.0; N, 28.0; S, 11.2%; $C_{12}H_{20}N_6OS$ requires: C, 48.6; H, 6.8; N, 28.4; S, 10.8%) n.m.r. analysis in DMSO-$d_6$ at 100 mHz:

| Assignment | Chemical Shift | Multiplicity | Integral Found | Integral Calc. |
|---|---|---|---|---|
| CH$_3$ | 2.13 | singlet | 3.0 | 3 |
| —SCH$_2$CH$_2$ | 2.59 | triplet | 2.6 | 2 |
| OCH$_3$ | 3.28 | singlet | } 9.5 | 9 |
| CH$_2$NHC(N)(NHCH$_2$CH$_2$) | 3.4 | multiplet | | |
| >—CH$_2$S | 3.68 | singlet | 2.0 | 2 |
| NHC(N)(NH) | 7.17 | multiplet | 1.6 | 2 |
| N>—H (N) | 7.47 | singlet | 0.7 | 1 |

EXAMPLE 12

N-Cyano-N'-(7-aminoheptyl)-N''-[2-((4-methyl-5-imidazolyl)methylthio)ethyl]guanidine

1,7-Diaminoheptane (5.2 g) was warmed gently until molten and to it was added N-cyano-N'-[2-((4-methyl-5-imidazolyl)methylthio)ethyl]-S-methylisothiourea (2.69 g). After stirring for 15 hours at room temperature the reaction mixture was extracted with ether to remove excess of the diamine starting material and then purified on a silica gel chromatographic colum, eluting with isopropanol to give the title compound (1.08 g), m.p. 84°–87° C.

(Found: C, 55.0; H, 8.2; N, 27.8; S, 9.0% $C_{16}H_{29}N_7S$ requires: C, 54.7; H, 8.3; N, 27.9; S, 9.1%).

EXAMPLE 13

N-Cyano-N'-(8-aminoethyl)-N''-[2-((4-methyl-5-imidazolyl)methylthio)ethyl]guanidine Using 1,8-diaminooctane as the starting material in the procedure of Example 12 yielded the title compound, m.p. 122°–124° C.

(Found: C, 56.0; H, 8.7; N, 26.6; S, 8.5% $C_{17}H_{31}N_7S$ requires: C, 55.9; H, 8.5; N, 26.8; S, 8.8%).

EXAMPLE 14

N-Cyano-N'-(10-aminodecyl)-N''-[2-((4-methyl-5-imidazolyl)methylthio)ethyl]guanidine Using 1,10-diamodecane as the starting material in the procedure of Example 12 yielded the title compound.

(Found: C, 58.2; H, 9.1; N, 24.8; S, 8.0% $C_{19}H_{35}N_7S$ requires: C, 58.0; H, 9.0; N, 24.9; S, 8.2%). n.m.r. analysis in DMSO-$d_6$ at 100 mHz:

| Assignment | Chemical Shift ( ) | Multiplicity | Integral Found | Integral Calc. |
|---|---|---|---|---|
| —(CH$_2$)$_8$— | 1.1–1.6 | multiplet | 16.0 | 16 |
| CH$_3$  | 2.13 | singlet | 3.0 | 3 |
| CH$_2$NH$_2$ + CH$_2$S | 2.58 | multiplet | — | 4 |
|  | 3.66 | singlet | 1.8 | 2 |
| >—CH$_2$S |  |  |  |  |
| NH$_2$ | 4.6 | multiplet | — | 2 |
|  | 7.41 | singlet | 1.3 | 1 |

EXAMPLE 15

Using 1,3-diaminopropane and 1,4-diaminobutane as the starting material in the procedure of Example 12 yields respectively N-cyano-N'-(3-aminopropyl)-N''-[2-((4-methyl-5-imidazolyl)methylthio)ethyl]guanidine and N-cyano-N'-(4-aminobutyl)-N''-[2-((4-methyl-5-imidazolyl)methylthio)ethyl]guanidine, m.p. 109°–111° C. (from acetonitrile/ether).

(Found: C, 50.7; H, 7.4; N, 31.8; S, 10.2% $C_{13}H_{23}N_7S$ required: C, 50.5; H, 7.5; N, 31.7; S, 10.4%).

EXAMPLE 16

N-Cyano-N'-(4-hydroxybutyl)-N''-[2-((4-methyl-5-imidazolyl)methylthio)ethyl]guanidine 4-Aminobutanol (2.7 g) and N-cyano-N'-[2-((4-methyl-5-imidazolyl)methylthio)ethyl]-S-methylisothiourea (4.05 g) were refluxed in ethanol (30 ml) for 4 hours. The reaction mixture was evaporated to yield an oil which was chromatographed on a silica gel column and eluted with chloroform and chloroform/methanol (20:1) to give the title compound as a colourless oil (1.8 g).

(Found: C, 50.4; H, 7.4; N, 26.8; S, 10.1% $C_{13}H_{22}N_6OS$ requires: C, 50.3; H, 7.2; N, 27.1; S, 10.3%).

| Assignment | Chemical Shift ( ) | multiplicity | Integral Found | Integral Calc. |
|---|---|---|---|---|
| —CH$_2$CH$_2$— | 1.45 | multiplet | 4.1 | 4 |
| CH$_3$  | 2.11 | singlet | 3.0(R) | 3 |
| SCH$_2$ | 2.57 | multiplet | 2.5 | 2 |
| >—CH$_2$S | 3.63 | singlet | 2.0 | 2 |
| NH—C—NH | 7.0 | multiplet | 2.1 | 2 |
|  | 7.41 | singlet | 0.9 | 1 |

EXAMPLE 17

N-(2-Aminoethyl)-N'-[2-((4-methyl-5-imidazolyl)methylthio)ethyl]guanidine trihydrochloride N-Cyano-N'-(2-aminoethyl)-N''-[2-((4-methyl-5-imidazolyl)methylthio)ethyl]guanidine (1.0 g) (see Example 10) and 1 N hydrochloric acid (20 ml) were refluxed together for 6 hours. Evaporation and recrystalisation from methanol/isopropanol gave the title compound (0.6 g), m.p. 195°–196° C.

(Found: C, 33.1; H, 6.3; N, 22.8; S, 8.8; Cl, 28.8% $C_{10}H_{20}N_6S.3HCl$ requires: C, 32.8; H, 6.3; N, 23.0; S, 8.8; Cl, 29.1%).

EXAMPLE 18

N-Allyl-N'-cyano-N''-[2-((4-methyl-5-imidazolyl)methylthio)ethyl]guanidine

Reaction of allylamine and N-cyano-N'-[2-((4-methyl-5-imidazolyl)methylthio)ethyl]-S-methylisothiourea by the procedure of Example 11 afforded the title compound, m.p. 113°–114° C. (from acetonitrile)

(Found: C, 51.6; H, 6.4; N, 30.1; S, 11.5% $C_{12}H_{18}N_6S$ requires: C, 51.8; H, 6.5; N, 30.2; S, 11.5%).

EXAMPLE 19

N-Cyano-N'-(2-methylaminoethyl)-N''-[2-((4-methyl-5-imidazolyl)methylthio)ethyl]guanidine N-Cyano-N'-[2-((4-methyl-5-imidazolyl)methylthio)ethyl]-S-methylisothiourea (5.4 g) and (2-aminoethyl)methylamine (25 ml) were mixed together and left for 15 hours at 20° C. Evaporation to dryness and azeotroping with acetonitrile to remove excess diamine gave a solid residue which was recrystallised from isopropanol to give the title compound (4.8 g), m.p. 146°–148° C.

(Found: C, 48.7; H, 7.3; N, 32.9; S, 10.9% $C_{12}H_{21}N_7S$ requires: C, 48.8; H, 7.2; N, 33.2; S, 10.9%).

EXAMPLE 20

N-Cyano-N'-(12-aminododecyl)-N''-[2-((4-methyl-5-imidazolyl)methylthio)ethyl]guanidine Using 1,12-diaminododecane as the starting material in the procedure of Example 12 yields the title compound.

EXAMPLE 21

A solution of 4-(4-aminobutyl)imidazole (from the dihydrobromide 3.6 g) and 1-nitro-2,2-bis-methylthioethylene (2.0 g) in acetonitrile (50 ml) is set aside at room temperature for 3 days. The product is chromatographed on a column of silica gel with elution by ethyl acetate to give 1-nitro-2-methylthio-2-[4-(4-imidazolyl)-butylamino]ethylene. Reaction of this methylthio compound with hydrazine hydrate in the procedure of Example 3 results in the production of 1-nitro-2-[4-(4-imidazolyl)butylamino]-2-hydrazinoethylene.

EXAMPLE 22

N-Amino-N'-[2-(4-methyl-5-imidazolylmethylthio)ethyl]thiourea

Hydrazine hydrate (0.01 mole) is added to a solution of 2-(4-methyl-5-imidazolylmethylthio)ethyl isothiocyanate (0.01 mole) in ethanol, and stirred for an hour at room temperature to give the title compound.

EXAMPLE 23

N-Dimethylamino-N'-[2-(4-methyl-5-imidazolylmethylthio)ethyl]thiourea

When N,N-dimethylhydrazine is used in place of hydrazine hydrate in the procedure of Example 22, and the mixture allowed to react for two days, the title compound is obtained.

EXAMPLE 24

N-Methylamino-N'-[2-(4-methyl-5-imidazolylmethylthio)ethyl]thiourea

N-tert butoxycarbonyl-N-methylhydrazine (0.01 mole) is added to a solution of 2-(4-methyl-5-imidazolylmethylthio)ethylisothiocyanate (0.01 mole) in ethanol and allowed to react for 24 hours at room temperature to give (N'-t-butoxycarbonyl-1-methyl)-1-[2-(4-methyl-5-imidazolylmethylthio)ethyl]thiosemicarbazide. When the latter is treated with conc. hydrochloric acid and then neutralized, the title compound is obtained.

EXAMPLE 25

Reaction of 4-(4-aminobutyl)imidazole with the following reactants:

N-cyano-N'-methoxy-S-methylisothiourea (see Example 1),
N-cyano-N'-(2,2,2-trifluoroethyl)-S-methylisothiourea (see Example 2) and
1-nitro-2-methylthio-2-(2,2,2-trifluoroethyl)aminoethylene (see Example 4) results respectively in the following products:

N-cyano-N'-methoxy-N''-[4-(4-imidazolyl)butyl]guanidine,
N-cyano-N'-(2,2,2-trifluoroethyl)-N''-[4-(4-imidazolyl)butyl]guanidine and
1-nitro-2-(2,2,2-trifluoroethylamino)-2-[4-(4-imidazolyl)butylamino]ethylene.

EXAMPLE 26

Reaction of 4-(4-aminobutyl)imidiazole with dimethylcyanodithiomidocarbonate gives N-cyano-N'-[4-(4-imidazolyl)butyl]-S-methylisothiourea which when reacted by the procedure of Example 12 with the following compounds:

1,2-diaminoethane,
1,8-diaminooctane,
1,12-diaminododecane and
2-hydroxyethylamine yields the following products respectively:

N-cyano-N'-(2-aminoethyl)-N''-[4-(4-imidazolyl)butyl]guanidine,
N-cyano-N'-(8-aminooctyl)-N''-[4-(4-imdiazolyl)butyl]guanidine,
N-cyano-N'-(12-aminododecyl)-N''-[4-(4-imidazolyl)butyl]guanidine and
N-cyano-N'-(2-hydroxyethyl)-N''-[4-(4-imidazolyl)butyl]guanidine.

EXAMPLE 27

Reaction of 2,2,2-trifluoroethylamino according to the procedure of Example 4 with 1-nitro-2-methylsulphinyl-2-methylthioethylene and then with the following amines:

(a) 3-chloro-2-[(2-aminoethyl)thiomethyl]pyridine,
(b) 3-bromo-2-[(2-aminoethyl)thiomethyl]pyridine,
(c) 3-hydroxy-2-[2-aminoethyl)thiomethyl]pyridine,
(d) 3-[(2-aminoethyl)thiomethyl]isothiazole,
(e) 4-methyl-5-[(2-aminoethyl)thiomethyl]oxazole,
(f) 3-[(2-aminoethyl)thiomethyl]isoxazole,
(g) 3-[(2-aminoethyl)thiomethyl]-1,2,4-triazole and
(h) 2-[(2-aminoethyl)thiomethyl]-1,3,4-thiadiazole
yields the following products:
(a) 1-nitro-2-(2,2,2-trifluoroethylamino)-2-[2-((3-chloro-2-pyridyl)methylthio)ethylamino]ethylene,
(b) 1-nitro-2-(2,2,2-trifluoroethylamino)-2-[2 ((3-bromo-2-pyridyl)methylthio)ethylamino]ethylene,
(c) 1-nitro-2-(2,2,2-trifluoroethylamino)-2-[2-((3-hydroxy-2-pyridyl)methylthio)ethylamino]ethylene,
(d) 1-nitro-2-(2,2,2-trifluoroethylamino)-2-[2-(3-isothiazolylmethylthio)ethylamino]ethylene,
(e) 1-nitro-2-(2,2,2-trifluoroethylamino)-2-[2-((4-methyl-5-oxazolyl)methylthio)ethylamino]ethylene,
(f) 1-nitro-2-(2,2,2-trifluoroethylamino)-2-[2-(3-isoxazolylmethylthio)ethylamino]ethylene,
(g) 1-nitro-2-(2,2,2-trifluoroethylamino)-2-[2-((3-(1,2,4-triazolyl)methylthio)ethylamino]ethylene and
(h) 1-nitro-2-(2,2,2-trifluoroethylamino)-2-[2-((2-(1,3,4-thiadiazolyl)methylthio)ethylamino]ethylene

EXAMPLE 28

Using methanolamine in place of ethanolamine in the procedure of Example 5 results in the production of N-cyano-N'-hydroxymethyl-N''-[2-((4-methyl-5-imidazolyl)methylthio)ethyl]guanidine

EXAMPLE 29

When in the procedure of Example 2 the amines (a) to (h) listed in Example 27 are used in place of 4-methyl-5-[(2-aminoethyl)thiomethyl]imidazole the following compounds are produced respectively:

(a) N-cyano-N'-(2,2,2-trifluoroethyl)-N''-[2-((3-chloro-2-pyridyl)methylthio)ethyl]guanidine,
(b) N-cyano-N'-(2,2,2-trifluoroethyl)-N''-[2-((3-bromo-2-pyridyl)methylthio)ethyl]guanidine,
(c) N-cyano-N'-(2,2,2-trifluoroethyl)-N''-[2-((3-hydroxy-2-pyridyl)methylthio)ethyl]guanidine,
(d) N-cyano-N'-(2,2,2-trifluoroethyl)-N''-[2-(3-isothiazolylmethylthio)ethyl]guanidine,
(e) N-cyano-N'-(2,2,2-trifluoroethyl)-N''-[2-((4-methyl-5-oxazolyl)methylthio)ethyl]guanidine,
(f) N-cyano-N'-(2,2,2-trifluoroethyl)-N''-[2-(3-isoxazolylmethylthio)ethyl]guanidine,
(g) N-cyano-N'-(2,2,2-trifluoroethyl)-N''-[2-((3-(1,2,4-triazolyl)methylthio)ethyl]guanidine and
(h) N-cyano-N'-(2,2,2-trifluoroethyl)-N''-[2-((2-(1,3,4-thiadiazolyl)methylthio)ethyl]guanidine.

Acid hydrolysis of these compounds results respectively in the corresponding disubstituted guanidine i.e., compounds of Formula I wherein X is NH.

EXAMPLE 30

Slow addition of a solution of each of the amines (a) to (b) of Example 27 in dry pyridine under nitrogen to a solution of dicyclohexylcarbodiimide and carbon disulphide in dry pyridine at −10° C. yields the corresponding isothiocyanate (of formula VII above). Reaction of this isothiocyanate with hydrazine hydrate according to the procedure of Example 22 yields respectively:

(a) N-amino-N'-[2-((3-chloro-2-pyridyl)methylthio)ethyl]thiourea,
(b) N-amino-N'-[2-((3-bromo-2-pyridyl)methylthio)ethyl]thiourea,
(c) N-amino-N'-[2-((3-hydroxy-2-pyridyl)methylthio)ethyl]thiourea,
(d) N-amino-N'-[2-(3-isothiazolylmethylthio)ethyl]thiourea,
(e) N-amino-N'-[2-((4-methyl-5-oxazolyl)methylthio)ethyl]thiourea,
(f) N-amino-N'-[2-(3-isoxazolylmethylthio)ethyl]thiourea,
(g) N-amino-N'-[2-((3-(1,2,4-triazolyl)methylthio)ethyl]thiourea and
(h) N-amino-N'-[2-((2-(1,3,4-thiadiazolyl)methylthio)ethyl]thiourea.

We claim:
1. A compound of the formula:

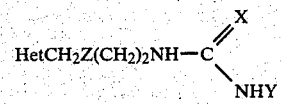

wherein X is N.CN; Y is di(lower alkyl)amino, lower alkoxy or phenylethyl; Z is sulphur or methylene; Het is an imidazole ring which is attached at a ring carbon and which ring is optionally substituted by lower alkyl, hydroxy, halogen or amino; provided that when Z is methylene, Y is not phenylethyl, or a pharmaceutically acceptable acid addition salt thereof.

2. A compound according to claim 1 wherein Het is imidazole optionally substituted by methyl, hydroxyl, chloro or bromo.

3. A compound according to claim 2 wherein Het is 4-methyl-5-imidazolyl.

4. A compound according to claim 1 wherein Y is lower alkoxy or phenylethyl.

5. A compound of claim 1, said compound being N-cyano-N'-methoxy-N''-[2-((4-methyl-5-imidazolyl)methylthio)ethyl]guanidine.

6. A compound of claim 1, said compound being N-cyano-N'-(2-phenylethyl)-N''-[2-((4-methyl-5-imidazolyl)methylthio)ethyl]guanidine.

7. A pharmaceutical composition to block histamine H$_2$-receptors comprising in an effective amount to block said receptors a compound according to claim 1 and a pharmaceutical diluent or carrier.

8. A method of blocking histamine H$_2$-receptors which comprises administering to an animal in need thereof in an effective amount to block said receptors a compound of claim 1.

* * * * *

UNITED STATES PATENT AND TRADEMARK OFFICE
CERTIFICATE OF CORRECTION

PATENT NO. : 4,333,946
DATED : June 8, 1982
INVENTOR(S) : Graham J. Durant, Charon R. Ganellin, Geoffrey R. Owen and Rodney C. Young It is certified that error appears in the above—identified patent and that said Letters Patent is hereby corrected as shown below:

Column 2, line 42, [2-methoxyethyl)-N"-[4-methyl- should read -- (2-methoxyethyl)-N"-[2-((4-methyl- -- .

Column 4, line 14, "action" should read -- actions -- .

Signed and Sealed this

Twenty-first Day of September 1982

[SEAL]

Attest:

GERALD J. MOSSINGHOFF

Attesting Officer    Commissioner of Patents and Trademarks